United States Patent
Russo et al.

(10) Patent No.: US 11,769,330 B2
(45) Date of Patent: Sep. 26, 2023

(54) SYSTEM AND METHOD FOR VIDEO ANALYTICS FOR THERMOGRAPHY PROCEDURE COMPLIANCE

(71) Applicant: MOTOROLA SOLUTIONS, INC., Chicago, IL (US)

(72) Inventors: Pietro Russo, Melrose, MA (US); Sven Rebien, Victoria (CA); Peter L. Venetianer, McLean, VA (US)

(73) Assignee: MOTOROLA SOLUTIONS, INC.

( * ) Notice: Subject to any disclaimer, the term of this patent is extended or adjusted under 35 U.S.C. 154(b) by 378 days.

(21) Appl. No.: 17/125,198

(22) Filed: Dec. 17, 2020

(65) Prior Publication Data

US 2022/0198195 A1 Jun. 23, 2022

(51) Int. Cl.
| | |
|---|---|
| G06V 20/52 | (2022.01) |
| G07C 9/28 | (2020.01) |
| G06V 20/40 | (2022.01) |
| G06V 10/143 | (2022.01) |
| A61B 5/01 | (2006.01) |

(52) U.S. Cl.
CPC .............. *G06V 20/52* (2022.01); *G06V 20/40* (2022.01); *G07C 9/28* (2020.01); *A61B 5/01* (2013.01); *G06V 10/143* (2022.01)

(58) Field of Classification Search
CPC .... G07C 9/00174; G06V 40/10; G06V 20/40; G06V 40/20; G16H 50/20; G16H 50/30; G01J 5/48; A61B 5/01; A61B 5/7275; A61B 5/746; A61B 5/0008
See application file for complete search history.

(56) References Cited

U.S. PATENT DOCUMENTS

| | | |
|---|---|---|
| 9,293,060 B2 | 3/2016 | Hanina et al. |
| 9,386,050 B2 | 7/2016 | Oswald |
| 10,271,017 B2 | 4/2019 | Tu et al. |
| 2012/0323589 A1 | 12/2012 | Udani |

(Continued)

FOREIGN PATENT DOCUMENTS

WO 2017167708 A1 10/2017

OTHER PUBLICATIONS

Anonymous: Thermal Imaging With Body Temperature Derivation and Facial Recognition for Educational/Nursery Child Fever Alert, ip.com Disclosure No. IPCOM000247666D, publication date: Sep. 26, 2016, 2 pages.

(Continued)

*Primary Examiner* — Margaret G Mastrodonato

(57) ABSTRACT

Disclosed is a process for implementing an automated analytics for insuring compliance for a thermographic protocol for subjects seeking a temperature check, perhaps for entrance or access to a controlled space or facility. The automated video analytics utilize one or more cameras to detect thermography compliance violations based on whether the subject is perspiring, dehydrated, recently consumed a beverage, has exposed skin, excessive clothing, the amount and type of activity before getting screened, and/or the external and internal temperatures at the controlled facility associated with the subject. Furthermore, the automated video analytics may create a non-compliance score and/or control a timer for a non-compliance detection. Also, short and long term collected data may be analyzed for compliance to guidelines.

20 Claims, 4 Drawing Sheets

(56) References Cited

U.S. PATENT DOCUMENTS

| | | |
|---|---|---|
| 2015/0094914 A1 | 4/2015 | Abreu |
| 2015/0105687 A1 | 4/2015 | Abreu |
| 2019/0354753 A1 | 11/2019 | Worrall |
| 2020/0142567 A1 | 5/2020 | Lim et al. |
| 2021/0302235 A1* | 9/2021 | Fox .......................... G01J 5/52 |
| 2021/0390804 A1* | 12/2021 | Rajamanickam ...... A61B 5/015 |
| 2021/0390812 A1* | 12/2021 | Chaurasia ................ G07C 9/27 |
| 2022/0157146 A1* | 5/2022 | Putterman ............ G06V 40/166 |

OTHER PUBLICATIONS

The International Search Report and the Written Opinion corresponding patent application No. PCT/US2021/061397 filed Dec. 1, 2021, dated Mar. 4, 2022, all pages.

* cited by examiner

SYSTEM AND METHOD FOR VIDEO ANALYTICS FOR THERMOGRAPHY PROCEDURE COMPLIANCE

BACKGROUND OF THE INVENTION

Thermographic imaging, including Long Wavelength InfraRed (LWIR) Imagers and Thermal Cameras, may be advantageously utilized for elevated temperature detection since it is a frictionless and efficient experience to allow for testing a subject at one or more screening stations. Various government agencies, including the United States Food and Drug Administration (FDA), have specific guidelines and compliance protocols that each subject being screened needs to follow for a sufficiently accurate electronic temperature measurement. However, present solutions fail to detect and/or enforce the guidelines and compliance protocols and thus lead to less dependable and accurate temperature readings.

BRIEF DESCRIPTION OF THE SEVERAL VIEWS OF THE DRAWINGS

In the accompanying figures similar or the same reference numerals may be repeated to indicate corresponding or analogous elements. These figures, together with the detailed description, below are incorporated in and form part of the specification and serve to further illustrate various embodiments of concepts that include the claimed invention, and to explain various principles and advantages of those embodiments.

Figure 1:
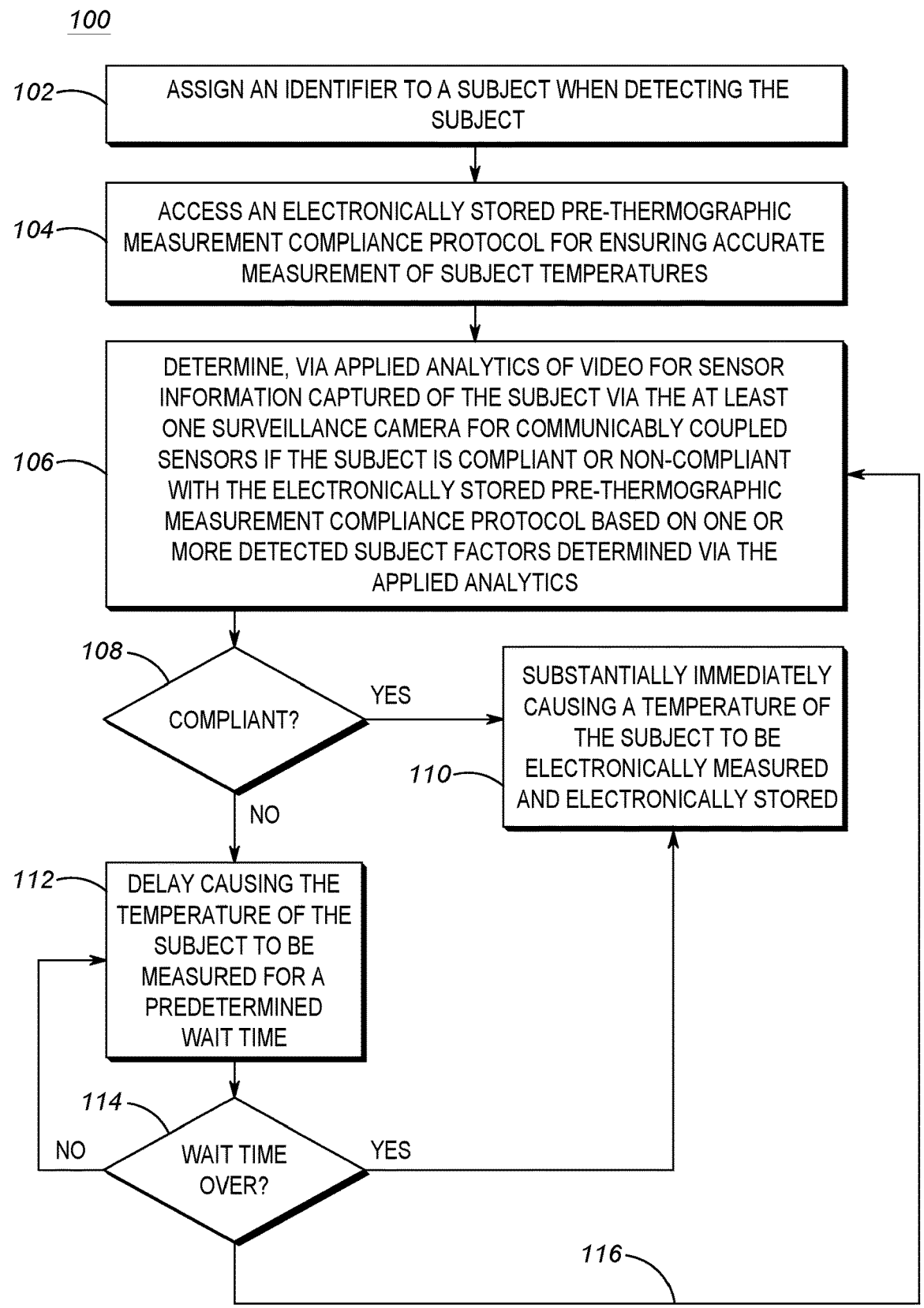
FIG. 1 is a flowchart of a method for video analytics for thermographic compliance protocols, in accordance with some examples.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

The apparatus and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION OF THE INVENTION

As discussed earlier, Thermographic Imaging, including LWIR Imagers and Thermal Cameras, may be utilized for elevated temperature detection since it provides a frictionless and efficient experience to allow for testing of one or more subjects (e.g., customers, clients, employees, contractors, human users, etc.). Also, various government agencies, including the United States Food and Drug Administration (FDA) has specific guidelines and compliance protocols that each subject being screened needs to follow in for a sufficiently accurate temperature measurement to be obtained via a thermographic imager. Present solutions fail to detect or enforce the guidelines and compliance protocols, and as a result, may produce inaccurate results. Thus, there exists a need for an improved method and system for automated video analytics for ensuring compliance for a thermographic measurement protocol that utilizes at least one surveillance camera in a surveillance system, and leverages automated image processing techniques to verify if a subject is in compliance with pre-thermographic measurement protocols prior to the subject's temperature being measured.

There are many factors to consider for an automated video analytics for ensuring compliance for a thermographic protocol for subjects seeking entrance or access to a controlled space or facility. For example, several factors to consider for the compliance protocol, and that could adversely affect the thermographic imaging system's ability to obtain accurate temperature measurements, could include, but are not limited to, whether the subject is perspiring, dehydrated, recently consumed a beverage, has exposed skin, is wearing excessive clothing, and the amount and type of activity engaged in before getting screened. Also, other factors could include the external and internal temperatures and humidity levels at the controlled facility associated with the subject, and/or the physical fitness level of the subject or subject prior to the screening. Based on the preceding factors, the following embodiments and examples depict systems and electronically implemented methods for determining compliance prior to taking the subject's temperature, and mitigation techniques once one or more same or different types of temperature-affecting factors are electronically detected. Also, short and long term collected data may be analyzed for compliance to guidelines. The following Figures and Description depict and explain utilization of one or more surveillance cameras with automated video analytics to detect pre-thermographic measurement compliance protocol violations.

In accordance with one example embodiment, a process for a video analytics utilizing at least one surveillance camera in a surveillance system for a thermographic compliance protocol for a subject includes: assigning, in an electronic memory by an electronic processing device, an identifier to a subject when detecting the subject; accessing, by the electronic processing device, an electronically stored pre-thermographic measurement compliance protocol for ensuring accurate measurement of subject temperatures; determining, by the electronic processing device via applied video analytics of video captured of the subject via the at least one surveillance camera, if the subject is compliant or non-compliant with the electronically stored pre-thermographic measurement compliance protocol based on one or more detected subject factors determined via the applied video analytics; when the electronic processing device determines that the subject is compliant with the electronically stored pre-thermographic measurement compliance protocol, substantially immediately causing a temperature of the subject to be electronically measured and electronically stored; and when the electronic processing device determines that the subject is non-compliant with the electronically stored pre-thermographic measurement compliance protocol, delaying causing the temperature of the subject to be electronically measured for a predetermined wait time, and after the predetermined wait time, causing the temperature of the subject to be electronically measured and electronically stored. In accordance with another example embodiment, a video analytics system for determining compliance with a thermographic compliance protocol for a subject, the system comprising an electronic processing device, communicatively coupled to one or more surveillance cameras, configured to: assign, in an electronic memory, an identifier to a subject when detecting the subject; access an electronically stored pre-thermographic measurement compliance protocol for ensuring accurate measurement of subject temperatures; determine, via applied video analytics of video captured of the subject via the at least one surveillance camera, if the subject is compliant or non-compliant with the electronically stored pre-thermographic measurement compliance protocol based on one or more detected subject factors determined via the applied video analytics; when the electronic processing device determines that the subject is compliant with the electronically stored pre-thermographic measurement compliance protocol, substantially immediately cause a temperature of the subject to be electronically measured and electronically stored; and when the electronic processing device determines that the subject is non-compliant with the electronically stored pre-thermographic measurement compliance protocol, delay causing the temperature of the subject to be electronically measured for a predetermined wait time, and after the predetermined wait time, cause the temperature of the subject to be electronically measured and electronically stored.

In accordance with a final example embodiment, a non-transient computer readable medium storing program instructions for causing a computer to perform a first set of functions, the first set of functions comprising: assign, in an electronic memory of the computer, an identifier to a subject when detecting the subject; access an electronically stored pre-thermographic measurement compliance protocol for ensuring accurate measurement of subject temperatures; determine, via applied video analytics of video captured of the subject via the at least one surveillance camera, if the subject is compliant or non-compliant with the electronically stored pre-thermographic measurement compliance protocol based on one or more detected subject factors determined via the applied video analytics; when the computer determines that the subject is compliant with the electronically stored pre-thermographic measurement compliance protocol, substantially immediately cause a temperature of the subject to be electronically measured and electronically stored; and when the computer determines that the subject is non-compliant with the electronically stored pre-thermographic measurement compliance protocol, delay causing the temperature of the subject to be electronically measured for a predetermined wait time, and after the predetermined wait time, cause the temperature of the subject to be electronically measured and electronically stored.

Attention is first directed to FIG. 1, which depicts a flowchart of a process 100 executed by an electronic processing device, as will be described in more detail with respect to FIG. 4, for video analytics-based pre-thermographic measurement compliance protocol determination, in accordance with some examples.

Process 100 begins at block 102, where a unique identifier is assigned by the electronic processing device to each subject detected by at least one camera in a surveillance system to which the electronic processing device is communicably coupled. The surveillance system includes at least one surveillance camera, which may include multiple converged or communicably coupled types of cameras, such as visible-light cameras, thermographic cameras, light field/depth ranging cameras, or other types of imaging cameras. At least one of the cameras in the surveillance system is a thermographic camera, such as a longwave infrared (LWIR) camera capable of electronically determining a temperature of one or more subjects from a distance. The visible-light and/or light field/depth ranging cameras, among other imaging devices such as RADAR devices, may be used for other purposes disclosed herein, such as identifying one or more detected subject factors as will be discussed in more detail below. The surveillance system may further include any additional number of communicably coupled sensors, such as temperature sensors (perhaps placed inside and/or outside of a building or facility), speed or acceleration sensors (perhaps for determining a speed or acceleration, and/or trajectory, or a subject), or other communicably coupled sensors useful for determining context and/or characteristics of a subject outside of his or her temperature.

When visible-light and/or light field/depth ranging cameras are available, such imaging devices may be used to uniquely (at least temporarily via a temporarily stored captured facial print, palm print, etc., if not globally unique by accessing a biometric database and uniquely identifying the subject by matching faces/biometric features via a facial/biometric recognition algorithm) identify the subject for purposes of tracking and confirming compliance with an electronically stored pre-thermographic measurement compliance protocol. Accordingly, the unique identifier may be a name, randomly assigned number, employee number, or some other unique identifier assigned to the subject for purposes of tracking and which, in some embodiments, may be used in conjunction with one or more other security factors (smart card, etc.) to provide access to a controlled space once compliance with the electronically stored pre-thermographic measurement compliance protocol is determined.

Subsequently, processing proceeds to block 104, where the electronic processing device accesses the electronically stored pre-thermographic measurement compliance protocol for ensuring accurate measurement of subject temperatures. The electronically stored pre-thermographic measurement compliance protocol may be stored at the electronic processing device, may be statically configured and stored at another database communicably coupled to the electronic processing device, or may be dynamically determined based on other contextual parameters such as a type of business or enterprise at which the communicably coupled surveillance system is installed (e.g., medical, warehouse, retail, etc.), among other possibilities.

Figure 2:
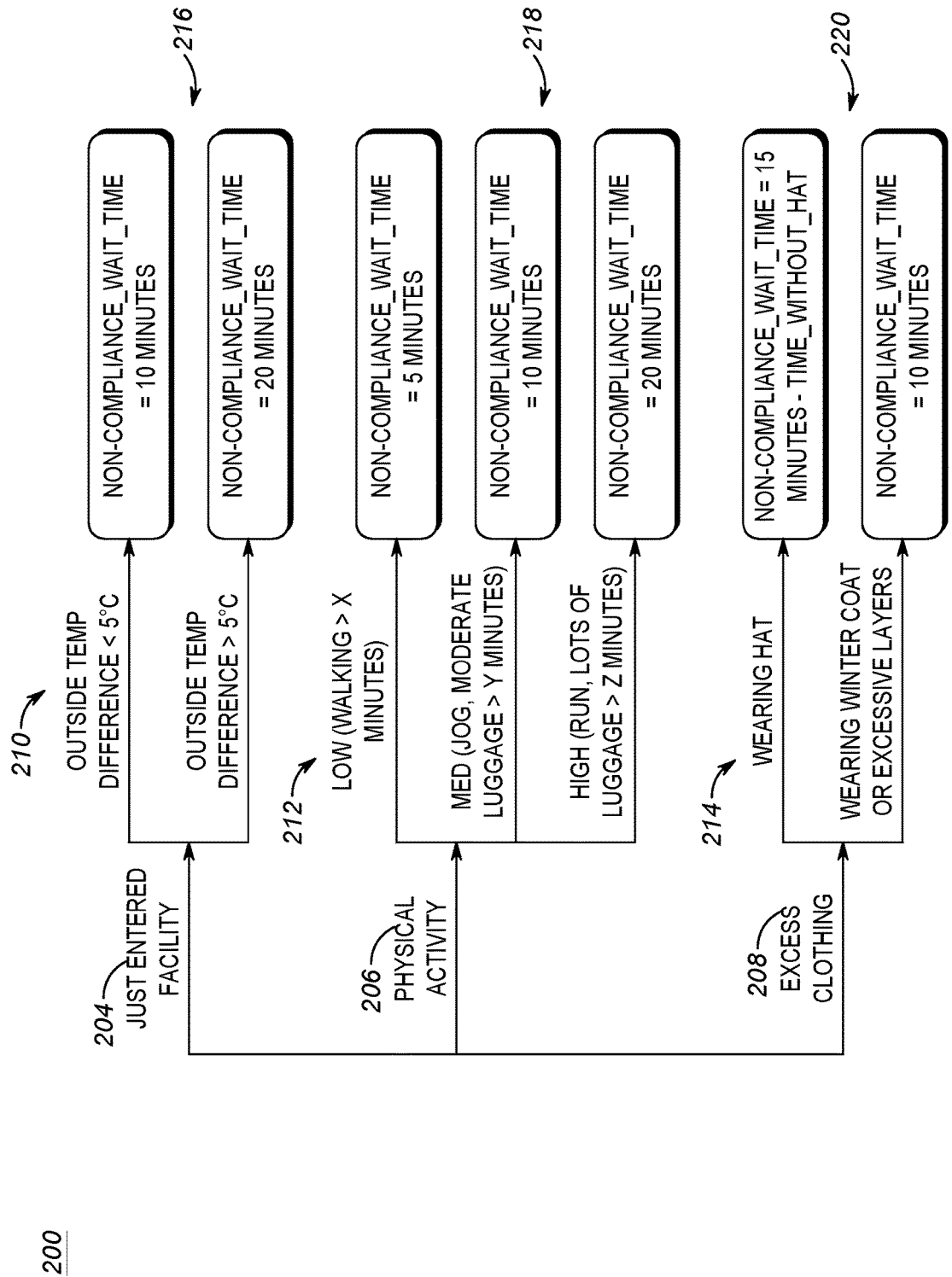
FIG. 2 is a diagram of an example of an electronically stored pre-thermographic measurement compliance protocol and associated predetermined wait time mapping, in accordance with some examples.

FIG. 2 provides an example of an electronically stored pre-thermographic measurement compliance protocol 200. The example electronically stored pre-thermographic measurement compliance protocol may be particularly stored/configured for a particular installation location or application, such as at a hospital or school, among other possibilities. Other electronically stored pre-thermographic measurement compliance protocols could be used for other installation locations or applications, and could include more or fewer, or different, pre-thermographic measurement compliance protocol parameters compared to that illustrated in FIG. 2. Furthermore, although FIG. 2 illustrates a hierarchical rule flow model of pre-thermographic measurement compliance protocol parameters for ease of description, in other embodiments, other data structures and computer readable databases or organizations could be used to electronically store enforceable pre-thermographic measurement compliance protocol parameters similar or different from that illustrated in FIG. 2.

As shown in FIG. 2, three categories of enforceable (via the surveillance system) pre-thermographic measurement compliance protocol parameters (also called subject factors elsewhere in this disclosure when these parameters are identified as being exhibited or associated with a subject awaiting temperature measurement) are shown, including a subject facility entry rule 204 (that reference sub-rules 210), a subject physical activity rule 206 (that reference sub-rules 212), and a subject excess clothing rule 208 (that reference sub-rules 214).

The subject facility entry rule 204 includes two enforceable sub-parameters 210 that evaluate (perhaps via thermographic cameras located inside and outside, or communicably coupled temperature sensors located inside and outside the facility where the surveillance system is installed and in which entry to a controlled space, for example, is dependent upon complying with the thermographic measurement compliance protocol) whether the first temperature measured outside the facility compared to the second temperature measured inside the facility has a less than 5 degree Celsius (or some other value between 1 and 50 degrees Celsius, or 1 and 25, or 1 and 10 degrees Celsius) difference, or has a greater than 5 degree Celsius (or some other value between 1 and 10 degrees Celsius) difference. As will be discussed in more detail with respect to block 112, different wait times may then be enforced for the subject before the subject's temperature is electronically measured for ultimately determining the subject's actual (or as close to actual as possible within reasonable time constraints) temperature (and/or for ultimately gaining access to a controlled space, among other possibilities). In this example, a longer subject wait time (20 minutes) is enforced when the detected outside temperature to inside temperature difference is greater than 5 degrees Celsius as compared to if the detected outside temperature to inside temperature difference is less than 5 degrees Celsius. Of course, other parameters could apply as well, such as whether the sun is shining or not, what the humidity is outside and inside, and other measureable and/or detectable parameters that may factor into a difference in temperature measurement when a subject transitions from an indoor environment to an outdoor environment and vice versa. And other temperature ranges and other wait times from 1 to 60 minutes could apply as well.

In some embodiments, additional surveillance system cameras or sensors may be leveraged to determine additional context around the subject, which may be used to contextually enforce (or not enforce) one or more pre-thermographic measurement compliance protocol parameters accessed at block 104. For example, in the case of the subject facility entry rule 204, additional surveillance system cameras or sensors may be used to track the subject's trajectory to see if the subject just recently entered the facility (e.g., within the last 20 minutes, or other time frame), and only apply the subject facility entry rule 204 when the subject's trajectory indicates the subject has travelled from outside to inside (otherwise, that rule 204 may be skipped, among other possibilities). Access control systems that control access from an outside environment to an indoor environment could additionally or alternatively provide trajectory information for use by the system, among other sensor or video input devices.

The subject physical activity rule 206 includes three enforceable sub-parameters 212 that evaluate (perhaps via visual light cameras located inside and/or outside the facility, or communicably coupled speed or acceleration sensors located inside and outside the facility where the surveillance system is installed, among other possibilities) a level of physical activity of the subject. As will be discussed in more detail with respect to block 112, different wait times may then be enforced for the subject before the subject's temperature is electronically measured for ultimately determining the subject's actual (or as close to actual as possible within reasonable time constraints) temperature (and/or for ultimately gaining access to a controlled space, among other possibilities). Physical activity or physical impact/strain may be judged based on an electronically detected speed, velocity, or acceleration of the subject (instantaneous or averaged over time), a visually electronically detected number of pieces of luggage/storage carried on the subject's person or under control by the subject, an electronically sensor detected weight of the subject (perhaps including luggage, etc.) or some other method.

In this example, a relatively longest subject wait time (20 minutes) is enforced when the detected physical activity is relatively highest (e.g., a threshold level of luggage pieces, 3, or weight, over 50 pounds, among other possibilities or a threshold velocity of over 5 mph), a relatively medium subject wait time (10 minutes) is enforced when the detected physical activity is in a defined mid-range (e.g., a threshold level of luggage pieces, 2, or weight, 20-50 pounds, among other possibilities or a threshold velocity of 3-5 mph), and a relatively shortest subject wait time (5 minutes) is enforced when the detected physical activity is relatively lowest (e.g., a threshold level of luggage pieces, 1, or weight, under 20 pounds, among other possibilities, or a threshold velocity of under 3 mph).

The subject excess clothing rule 208 includes two enforceable sub-parameters 214 that evaluate (perhaps via visual light cameras located inside and/or outside the facility, or communicably coupled subject user input electronic survey where the subject indicates what they are wearing currently or substantially immediately before taking the survey, among other possibilities) a level of excess clothing of the subject. As will be discussed in more detail with respect to block 112, different wait times may then be enforced for the subject before the subject's temperature is electronically measured for ultimately determining the subject's actual (or as close to actual as possible within reasonable time constraints) temperature (and/or for ultimately gaining access to a controlled space, among other possibilities).

In this example, a subject wait time of 15 minutes is enforced when the subject is detected or determined to be wearing a hat, and a subject wait time of 10 minutes is enforced when the subject is detected or determined to be wearing a winter coat or excessive multiple clothing layers.

Subsequently, processing proceeds to block 106, where the electronic processing device applies analytics to video and/or sensor inputs from the surveillance system associated with the subject and determines if the subject is compliant or non-compliant with the electronically stored pre-thermographic measurement protocol based on one or more detected subject factors (e.g., those pre-thermographic measurement compliance protocol parameters detected via the surveillance system associated with the subject awaiting temperature measurement) determined via the applied analytics. As explained earlier with respect to FIG. 2, the subject factors may be determined entirely via video (visual) analytics based on video received from one or more video cameras that are a part of the video surveillance system, via sensor information retrieved via electronically coupled to the electronic processing device, or some combination thereof, among other possibilities.

Figure 3:
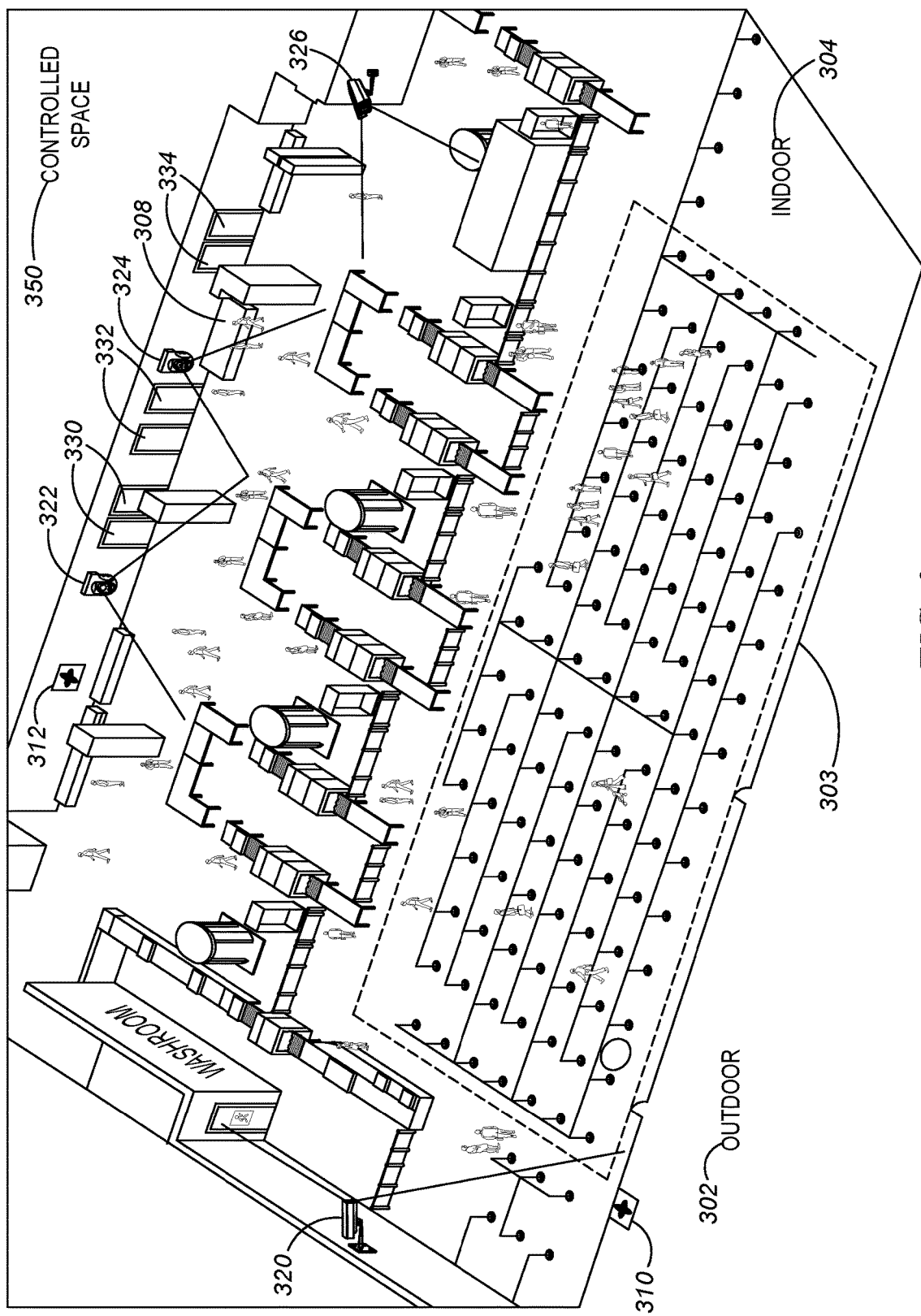
FIG. 3 is an example surveillance system for use with a pre-thermographic compliance screening station, in accordance with some examples.

As one particular example, attention is directed FIG. 3, which illustrates an example surveillance system 300 for use as a pre-thermographic compliance screening station, in accordance with some examples. The structure shown in FIG. 3 includes an outdoor area 302 and an indoor area 304 separated by a wall structure 303 having several doors included therein. An electronic processing device 308 configured to operate the surveillance system 300 is illustrated as disposed on premises with the surveillance system 300, but in other embodiments, may be located elsewhere, in the cloud, or distributed across on-premises and cloud components, among other possibilities.

Further included in surveillance system 300 are various distributed sensors, which include an outdoor temperature sensor 310 and an indoor temperature sensor 312, both communicably coupled to electronic computing device 308 (wiredly and/or wirelessly). Visual wavelength imaging cameras 320, 322, 324, and 326 are distributed across the surveillance system 300 and operate to detect subject factors determined via the applied video analytics. Any one or more of the visual wavelength imaging cameras may additionally or alternatively operate as a thermographic imaging (i.e., LWIR) camera capable of measuring a temperature of a subject. In the example of FIG. 3, it is assumed that cameras 322 and 324 include (or are) thermographic imaging cameras and may operate as pre-thermographic compliance screening stations to provide subject access to a controlled space 350 beyond doors 330, 332, 334, which may be partially or fully controlled by the surveillance system and may only open when the subject passes the temperature check.

In the example of FIG. 3, a particular subject 340 may have entered from the outdoor 302 area to the indoor 304 area and immediately proceeded towards doors 332 to enter controlled space 350. Camera 320 may have initially identified the subject 340 entering through a door in wall 303, and assigned a unique identifier to the subject (e.g., such as at block 102). After accessing the pre-thermographic measurement compliance protocol parameters illustrated in FIG. 2, let's further assume that the subject 340 walked in from outside, that the outside temperature to inside temperature difference is greater than 5 degrees, and the subject 340 is wearing a hat, and that it took the subject 4 minutes to walk to the thermographic screening station near thermographic camera 324 and removes his or her hat upon arrival at the screening station.

In one embodiment, the applied pre-thermographic measurement compliance protocol may take a maximum wait time (in parallel application of wait times) from all of those applicable wait times indicated in the parameters in FIG. 2 (e.g., 216-220), which in this case includes a non-compliance wait time of 20 minutes due to the temperature difference between inside and outside and a non-compliance wait time of 15 minutes once the subject removes his or her hat. Taking the 20 minute wait time from arriving indoors minus the 4 minute time to walk to the thermographic screening station near thermographic camera 324, leaves 16 minutes remaining before the subject's 320 temperature could be accurately and dependably electronically measured based on the compliance protocol. Furthermore, the 16 minutes remaining on the inside to outside temperature wait time is greater than the 15 minutes remaining on the wearing a hat wait time after it is removed, which after taking a maximum of the two, leaves the subject with a 16 minute wait time before compliance with the protocol is reached.

In other embodiments, the applied pre-thermographic measurement compliance protocol may take an aggregate wait time (sequential) from all of those applicable wait times indicated in the parameters in FIG. 2 (e.g., 216-220), which in this case includes a non-compliance wait time of 20 minutes due to the temperature difference between inside and outside and a non-compliance wait time of 15 minutes once the subject removes his or her hat. Taking the 20 minute wait time from arriving indoors minus the 4 minute time to walk to the thermographic screening station near thermographic camera 324, leaves 16 minutes remaining before the subject's 320 temperature could be accurately and dependably electronically measured based on the compliance protocol. Furthermore, the 15 minutes remaining on the wearing a hat wait time after it is removed would be added to the 16 minute wait time remaining for the inside to outside transition wait time, which results in a total of 31 minutes before compliance with the protocol is reached. Other examples are possible as well.

In still other embodiments, the particular wait time in the applied pre-thermographic measurement compliance protocol may indicate whether it is to be strictly applied independent of a measured subject's temperature, or whether the wait time is only applied if the subject's temperature is measured above a specified (for that parameter) or default subject temperature (such as 38.3 degrees C.). As one example, for the subject physical activity rule 206 (which generally tends to increase subject temperatures), even if the detected physical activity of the subject is high and a normal 20 minute wait time would be applied, if the measured subject's temperature is below the specified or default temperature, the subject may still be determined to be compliant at step 108. On the other hand, for the subject facility entry rule 204, if the outside temperature difference is above 5 degrees Celsius and the outside temperature is warmer than the inside temperature but the subject's temperature is still below the specified or default threshold, no wait time may be applied and the subject may still be determined to be compliant at step 108. However, if the outside temperature difference is above 5 degrees Celsius and the outside temperature is cooler than the inside temperature but the subject's temperature is still above the specified or default threshold, no wait time may be applied and the subject may still be determined to be non-compliant at step 108. Still further, if the outside temperature difference is above 5 degrees Celsius and the outside temperature is cooler than the inside temperature but the subject's temperature is below the specified or default threshold, the wait time may be strictly applied. Such additional contextual rules that define how the wait time is applied may be specified in the electronically stored pre-thermographic measurement compliance protocol 200 itself, or may be stored elsewhere at a location accessible to the electronic processing device.

Returning to FIG. 1, and subsequently, processing proceeds to block 108, where the electronic computing device applies the determination from block 106. In this example, and whether sequential or in parallel wait times are calculated, the subject 320 is non-compliant with the protocol at this time. Accordingly, processing would proceed to block 112, after which a loop would proceed at block 114 back to block 112 until sufficient time has passed to meet the calculated wait time from block 106 to make the subject compliant with the protocol wait time.

At block 114, and after the calculated wait time has passed, or at block 108 if the electronic computing device instead determines that the subject is compliant, processing proceeds to block 110, where the electronic processing device substantially immediately (e.g., within a processing delay time of several microseconds to several seconds) causes the thermographic imaging camera (e.g., camera 324 in FIG. 3) to take the subject's temperature and take some further action such as storing the temperature, alerting supervisory personnel (e.g., via transmitted electronic notification such as SMS or other text type message, or via an alert sound or communicatively coupled output display) if the subject's temperature is above a threshold (such as 100.4 degrees Fahrenheit), and/or providing access to a controlled space 350 dependent upon the subject's temperature being below the threshold, among other possibilities. In some embodiments, feedback to the subject 320 via some audible count down, visual display, or transmitted text messages with updated wait times may be provided to keep the subject 320 apprised of the remaining wait time before a temperature can be electronically measured.

Returning to block 114 of FIG. 1, in some optional embodiments, processing may proceed from block 114 via path 116 to block 106 in order to continue to track the subject during a wait time to see if any new or additional detected subject factors (e.g., those pre-thermographic measurement compliance protocol parameters detected via the surveillance system associated with the subject awaiting temperature measurement) determined via the applied analytics that may cause the calculated subject wait time to further change. As just one example, if the subject 320 of FIG. 3 puts his or her hat back on for some period of time, that may cause the excess clothing 208 parameter's timer 220 to reset and cause a further wait time to be applied, among other possibilities.

In some embodiments, at any one of blocks 102-108, a timer may be started to measure a time from at which the subject is first detected to have entered an area covered by the surveillance system, a time from at which the identifier was first assigned to the subject, a time from at which the subject was first determined to be non-compliant, or some other time there between to a current time.

Figure 4:
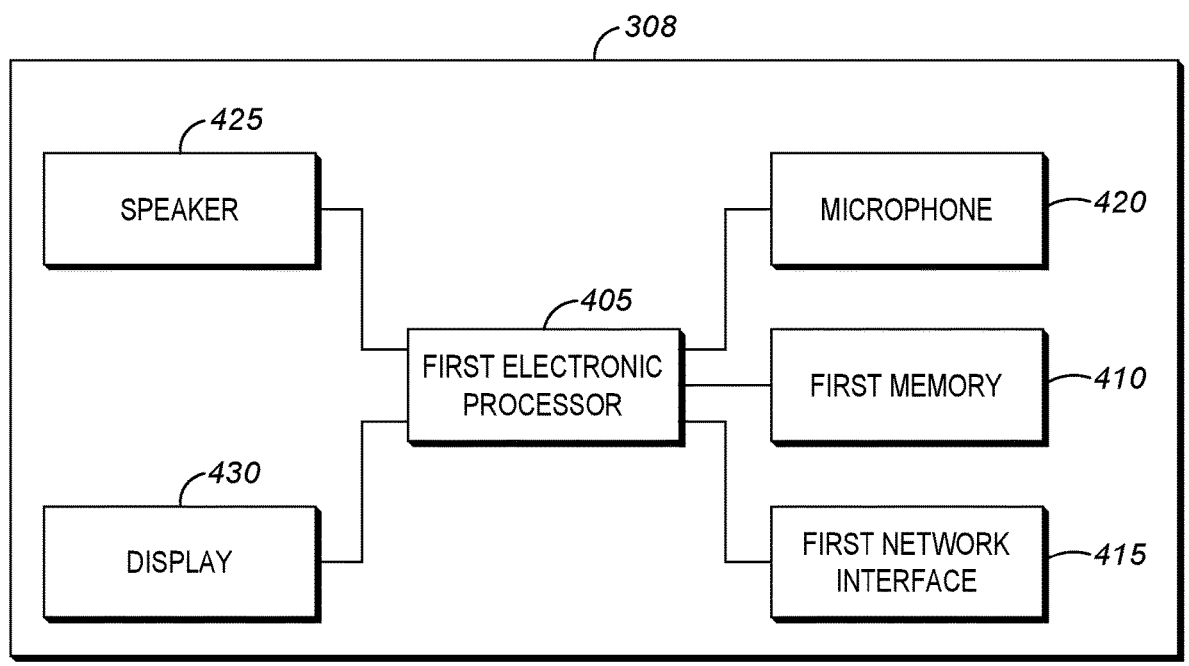
FIG. 4 is an exemplary computing device for processing incoming video and applying all or portions of the method set forth in FIG. 1, in accordance with some examples.

Attention is next directed to FIG. 4, which illustrates an electronic processing device for executing process 100 of FIG. 1, in accordance with some examples.

The processor and software instructions that are utilized to implement the previously described flowcharts and methods for computer vision and tracking could store and process one or more machine learning algorithms and/or deep learning algorithms of the software and may include, but are not limited to: a generalized linear regression algorithm; a random forest algorithm; a support vector machine algorithm; a gradient boosting regression algorithm; a decision tree algorithm; a generalized additive model; neural network algorithms; deep learning algorithms; evolutionary programming algorithms; Bayesian inference algorithms, reinforcement learning algorithms, and the like.

However, generalized linear regression algorithms, random forest algorithms, support vector machine algorithms, gradient boosting regression algorithms, decision tree algorithms, generalized additive models, and the like may be preferred over neural network algorithms, deep learning algorithms, evolutionary programming algorithms, and the like, in some public safety environments. However, any suitable computer vision, machine learning algorithm, and/or deep learning algorithm is within the scope of present examples. As discussed earlier, the algorithms would analyze the video received from the camera(s) and analyze based on the associated compliance protocol.

FIG. 4 is a block diagram of an electronic processing device 308 according to one example embodiment. In the embodiment illustrated, electronic processing device 308 includes a first electronic processor 405 (for example, a microprocessor or other electronic device). The first electronic processor 405 includes input and output interfaces (not shown) and is electrically coupled to a first memory 410, a first network interface 415, a microphone 420, a speaker 425, and a display 430. In some embodiments, the electronic processing device 308 includes fewer or additional components in configurations different from that illustrated in FIG. 4. For example, the electronic processing device 308 may additionally include a push-to-talk button and/or a camera, either or both of which may be used to allow the call taker/dispatcher to participate in one of the audio and/or audio/video calls forwarded to the electronic processing device 308, or to review video generated by cameras in the surveillance system 300. As another example, the electronic processing device 308 may include one or more additional input devices such as a computer mouse and/or a keyboard that receive inputs from a user of the electronic processing device 308. In some embodiments, the electronic processing device 308 performs functionality in addition to or other than the functionality described below. In still further embodiments, the electronic processing device 308 may not include a network interface 415, microphone 420, display 430, and/or speaker 425.

The first memory 410 may include read only memory (ROM), random access memory (RAM), other non-transitory computer-readable media, or a combination thereof. The first electronic processor 405 is configured to receive instructions and data from the first memory 410 and execute, among other things, the instructions. In particular, the first electronic processor 405 executes instructions stored in the first memory 410 to perform the methods described herein, including but not limited to the electronic processing device 308 operations described with respect to FIG. 1 and its associated text. In some embodiments, some or all of the electronic processor 405 and the first memory 410 is implemented on devices located at an on-premises device such as the electronic computing device 308 shown in FIG. 3, while in other embodiments, some or all of the electronic processor 405 and the first memory 410 may be located at a remote cloud-computer cluster accessible via one or more wired and/or wireless networks.

The first memory 410 may further store, permanently or temporarily, all or portions of one or more of the databases illustrated, for example, in FIG. 2 and associated text, among other electronically created, modified, and/or stored content.

The first network interface 415 electronically sends and receives data to and from the electronic devices illustrated in the surveillance system 300 in FIG. 3, among other devices. In some embodiments, the first network interface 415 includes one or more transceivers for wirelessly communicating with the electronic devices illustrated in the surveillance system 300 in FIG. 3. Alternatively or in addition, the first network interface 415 may include a connector or port for receiving a wired connection for communicating with the electronic devices illustrated in the surveillance system 300 in FIG. 3, such as an Ethernet cable. The first electronic processor 405 may receive one or more sensor or video data feeds through the first network interface 415 (for example, data feeds generated by one or more of cameras 320, 322, 324, and/or 326).

The first electronic processor 405 may output one or more results of the compliance determination and/or one or more results of the subject temperature measurement (relative to a threshold) to a connected display 430, speaker 425, or to some other electronic recipient via network interface 415, among other possibilities.

The display 430 displays images, video, text, and/or data to the subject, a supervisor, or other individual. The display 430 may be a liquid crystal display (LCD) screen or an organic light emitting display (OLED) display screen. In some embodiments, a touch sensitive input interface may be incorporated into the display 430 as well, allowing the subject or supervisor to interact with content provided on the display 430. In some embodiments, the speaker 425 and the display 430 are referred to as output devices that present data feeds to a subject or supervisor at the electronic computing device 308. In some embodiments, the microphone 420, a computer mouse, and/or a keyboard or a touch-sensitive display are referred to as input devices that receive input from a subject or supervisor at the electronic computing device 308

Hence, provided herein is a system and process for video analytics for an improved temperature measurement compliance protocol using an electronic surveillance system.

In the foregoing specification, specific embodiments have been described. However, one of ordinary skill in the art appreciates that various modifications and changes may be made without departing from the scope of the invention as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, Recommend, or essential features or elements of any or all the claims. The invention is defined solely by the appended claims including any amendments made during the pendency of this application and all equivalents of those claims as issued.

In this document, language of "at least one of X, Y, and Z" and "one or more of X, Y and Z" may be construed as X only, Y only, Z only, or any combination of two or more items X, Y, and Z (e.g., XYZ, XY, YZ, XZ, and the like). Similar logic may be applied for two or more items in any occurrence of "at least one . . . " and "one or more . . . " language.

Moreover, in this document, relational terms such as first and second, top and bottom, and the like may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

It will be appreciated that some embodiments may be comprised of one or more generic or specialized processors (or "processing devices") such as microprocessors, digital signal processors, customized processors and field programmable gate arrays (FPGAs) and unique stored program instructions (including both software and firmware) that control the one or more processors to implement, in conjunction with certain non-processor circuits, some, most, or all of the functions of the method and/or apparatus described herein. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used.

Moreover, an embodiment may be implemented as a computer-readable storage medium having computer readable code stored thereon for programming a computer (e.g., comprising a processor) to perform a method as described and claimed herein. Examples of such computer-readable storage mediums include, but are not limited to, a hard disk, a CD-ROM, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it may be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

We claim:

1. A method for a video analytics utilizing at least one surveillance camera in a surveillance system for a thermographic compliance protocol for a subject, the method comprising:

assigning, in an electronic memory by an electronic processing device, an identifier to a subject when detecting the subject;

accessing, by the electronic processing device, an electronically stored pre-thermographic measurement compliance protocol for ensuring accurate measurement of subject temperatures, the electronically stored pre-thermographic measurement compliance protocol identifying one or more thermographic measurement wait times corresponding to one or more subject factors indicating non-compliance with the electronically stored pre-thermographic measurement compliance protocol;

determining, by the electronic processing device via applied video analytics of video captured of the subject via the at least one surveillance camera, if the subject is compliant or non- compliant with the electronically stored pre-thermographic measurement compliance protocol based on one or more detected subject factors determined via the applied video analytics;

when the electronic processing device determines that the subject is compliant with the electronically stored pre-thermographic measurement compliance protocol, substantially immediately causing a temperature of the subject to be electronically measured and electronically stored; and when the electronic processing device determines that the subject is non-compliant with the electronically stored pre-thermographic measurement compliance protocol, determining a thermographic measurement wait time based on (i) the one or more detected subject factors and (ii) the electronically stored pre-thermographic measurement compliance protocol, delaying causing the temperature of the subject to be measured for the predetermined thermographic measurement wait time, and after the predetermined thermographic measurement wait time, causing the temperature of the subject to be electronically measured and electronically stored.

2. The method of claim 1, wherein the electronically stored pre-thermographic measurement compliance protocol identifies a threshold level of physical activity by the subject, and the one or more detected subject factors includes a physical activity level for the subject above the threshold minimum level of physical activity.

3. The method of claim 1, wherein the electronically stored pre-thermographic measurement compliance protocol identifies a threshold level of hydration for the subject, and the one or more detected subject factors includes a hydration level for the subject below the threshold minimum level of hydration.

4. The method of claim 1, wherein the electronically stored pre-thermographic measurement compliance protocol identifies a threshold maximum level of clothing for the subject, and the one or more detected subject plurality of detected factors includes an excessive clothing level for the subject above the threshold maximum level of clothing.

5. The method of claim 1, wherein the electronically stored pre-thermographic measurement compliance protocol identifies a threshold maximum level of exposed skin for the subject, and the one or more detected subject factors includes an exposed skin level for the subject above the threshold maximum level of exposed skin.

6. The method of claim 1, wherein the electronically stored pre-thermographic measurement compliance protocol identifies a threshold maximum temperature differential between an external environment where the subject was previously detected via the surveillance system and an internal environment where the subject is currently detected via the surveillance system, and the one or more detected subject factors includes a temperature differential between the external environment, where the subject was previously detected via the surveillance system, and the internal environment, where the subject is currently detected via the surveillance system, that is above the threshold maximum temperature differential.

7. The method of claim 1, wherein causing the temperature of the subject to be electronically measured comprises causing, by the electronic processing device, a thermal camera to take the temperature of the subject.

8. The method of claim 1, wherein the predetermined thermographic measurement wait time is variable based at least in part on one or both of a type of the detected subject factor determined to be non-compliant with the electronically stored pre-thermographic measurement compliance protocol and a number of detected subject factors determined to be non-compliant with the electronically stored pre-thermographic measurement compliance protocol.

9. The method of claim 8, further comprising:
calculating, by the electronic processing device, a compliance score based on the type and number of detected subject factors determined to be non-compliant with the electronically stored pre-thermographic measurement compliance protocol, wherein determining the thermographic measurement wait time comprises determining the thermographic measurement wait time based on the compliance score.

10. The method of claim 1, further comprising:
while delaying causing the temperature of the subject to be measured for the determined thermographic measurement wait time, preventing the subject from passing through an electronically controlled access mechanism to access a controlled space.

11. The method of claim 10, further comprising:
while delaying causing the temperature of the subject to be measured for the predetermined thermographic measurement wait time, providing one or both of a visual and auditory notification to the subject of the determined thermographic measurement wait time.

12. The method of claim 1, further comprising:
after causing the temperature of the subject to be electronically measured, comparing the subject's measured temperature to a threshold temperature value, and responsive to determining that the subject's measured temperature is below the threshold temperature value, electronically controlling, via the electronic processing device, an electronically controlled access mechanism to allow the subject to newly access a controlled space that was previously inaccessible to the subject.

13. A video analytics system for determining compliance with a thermographic compliance protocol for a subject, the system comprising an electronic processing device, communicatively coupled to one or more surveillance cameras, configured to:
assign, in an electronic memory, an identifier to a subject when detecting the subject;
access an electronically stored pre-thermographic measurement compliance protocol for ensuring accurate measurement of subject temperatures, the electronically stored pre-thermographic measurement compliance protocol identifying one or more thermographic measurement wait times corresponding to one or more subject factors indicating non-compliance with the electronically stored pre-thermographic measurement compliance protocol;
determine, via applied video analytics of video captured of the subject via the at least one surveillance camera, if the subject is compliant or non-compliant with the electronically stored pre-thermographic measurement compliance protocol based on one or more detected subject factors determined via the applied video analytics;

when the electronic processing device determines that the subject is compliant with the electronically stored pre-thermographic measurement compliance protocol, substantially immediately cause a temperature of the subject to be electronically measured and electronically stored; and when the electronic processing device determines that the subject is non-compliant with the electronically stored pre-thermographic measurement compliance protocol, determine a thermographic measurement wait time based on (i) the one or more detected subject factors and (ii) the electronically stored pre-thermographic measurement compliance protocol, delay causing the temperature of the subject to be measured for the predetermined thermographic measurement wait time, and after the determined thermographic measurement wait time, cause the temperature of the subject to be electronically measured and electronically stored.

14. The system of claim 13, wherein the electronically stored pre-thermographic measurement compliance protocol identifies a threshold minimum level of physical activity by the subject, and the one or more detected subject factors includes a physical activity level for the subject above the threshold minimum level of physical activity.

15. The system of claim 13, wherein the electronically stored pre-thermographic measurement compliance protocol identifies a threshold minimum level of hydration for the subject, and the one or more detected subject factors includes a hydration level for the subject below the threshold minimum level of hydration.

16. The system of claim 13, wherein the electronically stored pre-thermographic measurement compliance protocol identifies a threshold maximum level of clothing for the subject, and the one or more detected subject factors includes an excessive clothing level for the subject above the threshold maximum level of clothing.

17. The system of claim 13, wherein the electronically stored pre-thermographic measurement compliance protocol identifies a threshold maximum temperature differential between an external environment where the subject was previously detected and an internal environment where the subject is currently detected, and the one or more detected subject factors includes a temperature differential between the external environment where the subject was previously detected and the internal environment where the subject is currently detected environment above the threshold maximum temperature differential.

18. The system of claim 13, wherein the predetermined thermographic measurement wait time is variable based at least in part on one or both of a type of the detected subject factor determined to be non-compliant with the electronically stored pre-thermographic measurement compliance protocol and a number of detected subject factors determined to be non-compliant with the electronically stored pre-thermographic measurement compliance protocol.

19. The system of claim 13, the electronic processing device further configured to:

while delaying causing the temperature of the subject to be measured for the predetermined thermographic measurement wait time, prevent the subject from passing through an electronically controlled access mechanism to access a controlled space.

20. A non-transient computer readable medium storing program instructions for causing a computer to perform a first set of functions, the first set of functions comprising:

assigning, in an electronic memory of the computer, an identifier to a subject when detecting the subject;

accessing an electronically stored pre-thermographic measurement compliance protocol for ensuring accurate measurement of subject temperatures, the electronically stored pre-thermographic measurement compliance protocol identifying one or more thermographic measurement wait times corresponding to one or more subject factors indicating non-compliance with the electronically stored pre-thermographic measurement compliance protocol;

determining, via applied video analytics of video captured of the subject via the at least one surveillance camera, if the subject is compliant or non-compliant with the electronically stored pre-thermographic measurement compliance protocol based on one or more detected subject factors determined via the applied video analytics;

when the computer determines that the subject is compliant with the electronically stored pre-thermographic measurement compliance protocol, substantially immediately causing a temperature of the subject to be electronically measured and electronically stored; and when the computer determines that the subject is non-compliant with the electronically stored pre-thermographic measurement compliance protocol, determining a thermographic measurement wait time based on (i) the one or more detected subject factors and (ii) the electronically stored pre-thermographic measurement compliance protocol, delaying causing the temperature of the subject to be measured for the determined thermographic measurement wait time, and after the determined thermographic measurement wait time, causing the temperature of the subject to be electronically measured and electronically stored.

* * * * *